(12) United States Patent
Bae et al.

(10) Patent No.: US 11,175,278 B2
(45) Date of Patent: Nov. 16, 2021

(54) BIO-INFORMATION ESTIMATION APPARATUS AND BIO-INFORMATION ESTIMATION METHOD

(71) Applicant: SAMSUNG ELECTRONICS CO., LTD., Suwon-si (KR)

(72) Inventors: Sang Kon Bae, Seongnam-si (KR); Eui Seok Shin, Yongin-si (KR); So Young Lee, Daejeon (KR); Yun S. Park, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 947 days.

(21) Appl. No.: 15/897,921

(22) Filed: Feb. 15, 2018

(65) Prior Publication Data

US 2019/0154656 A1     May 23, 2019

(30) Foreign Application Priority Data

Nov. 20, 2017   (KR) .................. 10-2017-0155055

(51) Int. Cl.
| | | |
|---|---|---|
| G01N 33/49 | (2006.01) | |
| A61B 5/145 | (2006.01) | |
| A61B 5/00 | (2006.01) | |
| A61B 5/01 | (2006.01) | |
| G01N 21/31 | (2006.01) | |
| G01N 21/3577 | (2014.01) | |
| G01N 21/65 | (2006.01) | |

(52) U.S. Cl.
CPC ............ *G01N 33/49* (2013.01); *A61B 5/0075* (2013.01); *A61B 5/01* (2013.01); *A61B 5/14532* (2013.01); *G01N 21/3103* (2013.01); *G01N 21/3577* (2013.01); *G01N 21/65* (2013.01)

(58) Field of Classification Search
CPC ............... G01N 33/49; G01N 21/3103; G01N 21/3577; G01N 21/65; A61B 5/01; A61B 5/14532
USPC ........................................................ 703/11
See application file for complete search history.

(56) References Cited

U.S. PATENT DOCUMENTS

| | | | |
|---|---|---|---|
| 4,436,812 A | 3/1984 | Endoh et al. | |
| 5,028,787 A | 7/1991 | Rosenthal et al. | |
| 5,068,536 A | 11/1991 | Rosenthal | |
| 5,077,476 A | 12/1991 | Rosenthal | |
| 5,086,229 A | 2/1992 | Rosenthal et al. | |
| 5,204,532 A | 4/1993 | Rosenthal | |
| 5,218,207 A | 6/1993 | Rosenthal | |
| 5,237,178 A | 8/1993 | Rosenthal et al. | |
| 5,361,758 A | 11/1994 | Hall et al. | |
| 5,362,966 A | 11/1994 | Rosenthal et al. | |
| 5,365,066 A | 11/1994 | Krueger, Jr. et al. | |
| 5,436,455 A | 7/1995 | Rosenthal et al. | |
| 5,438,201 A | 8/1995 | Rosenthal et al. | |
| 5,574,283 A | 11/1996 | Quintana | |
| 5,576,544 A | 11/1996 | Rosenthal | |
| 6,066,847 A | 5/2000 | Rosenthal | |
| 6,992,816 B2 | 1/2006 | Chung et al. | |
| 7,041,468 B2 | 5/2006 | Drucker et al. | |
| 7,460,895 B2 | 12/2008 | Arnold et al. | |
| 8,140,139 B2 | 3/2012 | Grata et al. | |
| 9,037,206 B2 | 5/2015 | Grata et al. | |
| 2002/0038080 A1 | 3/2002 | Makarewicz et al. | |
| 2002/0123677 A1 | 9/2002 | Miki et al. | |
| 2005/0036146 A1 | 2/2005 | Braig et al. | |
| 2005/0187438 A1 | 8/2005 | Xie | |
| 2010/0312176 A1 | 12/2010 | Lauer et al. | |
| 2011/0132774 A1 | 6/2011 | Aum | |
| 2012/0010477 A1 | 1/2012 | Amano et al. | |
| 2012/0166092 A1 | 6/2012 | Maruo | |
| 2015/0297144 A1 | 10/2015 | Kamimura | |
| 2016/0174853 A1 | 6/2016 | Cho et al. | |
| 2016/0235375 A1 | 8/2016 | Kim et al. | |

FOREIGN PATENT DOCUMENTS

| | | |
|---|---|---|
| JP | 57-97431 A | 6/1982 |
| JP | 2000-60803 A | 2/2000 |
| JP | 2010-540133 A | 12/2010 |
| KR | 1994-7001541 A | 5/1994 |
| KR | 10-2002-0055364 A | 7/2002 |
| KR | 10-0694598 B1 | 3/2007 |
| KR | 10-2008-0026159 A | 3/2008 |
| KR | 10-2009-0118314 A | 11/2009 |
| KR | 10-2012-0095037 A | 8/2012 |
| KR | 10-1500710 B1 | 3/2015 |
| KR | 10-2015-0082455 A | 7/2015 |
| KR | 10-2016-0032789 A | 3/2016 |

(Continued)

OTHER PUBLICATIONS

Communication dated Sep. 12, 2018, issued by the European Patent Office in counterpart European Application No. 18162754.8.

*Primary Examiner* — Jerry Lin
(74) *Attorney, Agent, or Firm* — Sughrue Mion, PLLC

(57) ABSTRACT

Provided is an apparatus for estimating bio-information in a non-invasive manner. According to an exemplary embodiment, the bio-information estimation apparatus includes: a spectrum measurer configured to measure a spectrum of light reflected from an object; a temperature measurer configured to measure the temperature of the object while the spectrum measurer measures the spectrum of light reflected from the object; and a processor configured to calculate a spectrum correction factor, including one or more of a correction factor of a gain, a constant, and a slope, based on the measured temperature of the object, and to adjust the measured spectrum by using the calculated correction factor.

16 Claims, 17 Drawing Sheets

(56) References Cited

FOREIGN PATENT DOCUMENTS

| KR | 10-2016-0075230 A | 6/2016 |
| KR | 10-2016-0100140 A | 8/2016 |
| KR | 10-1716663 B1 | 3/2017 |

BIO-INFORMATION ESTIMATION APPARATUS AND BIO-INFORMATION ESTIMATION METHOD

CROSS-REFERENCE TO RELATED APPLICATION(S)

This application claims priority from Korean Patent Application No. 10-2017-0155055, filed on Nov. 20, 2017, in the Korean Intellectual Property Office, the entire disclosure of which is incorporated herein by reference for all purposes.

BACKGROUND

1. Field

Apparatuses and methods consistent with exemplary embodiments relate estimating bio-information in a non-invasive manner, and more particularly to technology for estimating bio-information by considering a spectrum change according to a temperature change.

2. Description of the Related Art

Diabetes is a chronic disease that is difficult to treat and can lead to various complications. It is required to check a patient's blood sugar levels regularly to prevent complications. In addition, if a person with diabetes is injected with insulin, the person needs to check blood sugar levels to prepare for low blood sugar and to control the insulin injection amount. Invasive methods are commonly used to measure blood sugar levels. However, while such invasive methods result in highly reliable measurements, they are painful and cumbersome and may cause infections when a sample of blood is taken using a syringe. For this reason, research is being conducted on a method of estimating bio-information, such as blood glucose, in a non-invasive manner by analyzing a spectrum using a spectrometer without directly drawing blood.

SUMMARY

According to an aspect of an exemplary embodiment, there is provided a bio-information estimation apparatus including: a spectrum measurer configured to measure a spectrum of light reflected from an object; a temperature measurer configured to measure the temperature of the object while the spectrum measurer measures the spectrum of light reflected from the object; and a processor configured to calculate a spectrum correction factor, including one or more of a correction factor of a gain, a constant, and a slope, based on the measured temperature of the object, and to adjust the measured spectrum by using the calculated correction factor.

The spectrum measurer may include: a light source configured to emit light onto the object; and a detector configured to detect light reflected from the object to measure a spectrum.

The spectrum measurer may measure the spectrum by using at least one of Infrared spectroscopy and Raman spectroscopy.

Once temperature is measured by the temperature measurer, the processor may calculate the correction factor by inputting the measured temperature into a correction factor calculation formula.

The correction factor calculation formula may be obtained by analyzing a correlation between a spectrum, which is measured from light reflected form the object at a reference or a standard solution at a reference temperature, and a spectrum measured from light reflected from the object at a temperature different from the reference temperature.

Further, the bio-information estimation apparatus may further include an output part configured to output alarm information in response to the temperature measurer failing to measure temperature or the measured temperature falling outside a threshold range while the spectrum is measured.

Once the correction factor is calculated, the processor may adjust the gain, constant, and slope of the measured spectrum by the calculated correction factor of the gain, constant, and slope in consideration of a change tendency of a gain, a constant, and a slope of a spectrum according to a change tendency of the measured temperature as compared to the reference temperature.

Once the measured spectrum is adjusted, the processor may estimate bio-information by applying a bio-information measuring model to the adjusted spectrum.

The bio-information may include one or more of blood glucose, cholesterol, triglyceride, protein, and uric acid.

In addition, the bio-information estimation apparatus may further include an output part configured to output one or more of the measured spectrum, the measured temperature, the estimated bio-information, and warning information generated in response to the estimated bio-information.

According to an aspect of another exemplary embodiment, there is provided a bio-information estimation method, the method including: measuring a spectrum of light reflected from an object; measuring a temperature of the object while the spectrum is measured from the object; calculating a spectrum correction factor, including a correction factor of one or more of a gain, a constant, and a slope, based on the measured temperature of the object; and adjusting the measured spectrum by using the calculated correction factor.

The calculating of the correction factor may include, once temperature of the object is measured, calculating the correction factor by inputting the measured temperature into a correction factor calculation formula.

The correction factor calculation formula may be obtained by analyzing a correlation between a spectrum, which is measured at a reference temperature from a standard solution including a component related to the object or the bio-information, and a spectrum measured according to a temperature change.

The measuring of the temperature may include outputting alarm information in response to a failure to measure temperature or the measured temperature falling outside a threshold range.

The adjusting of the spectrum may include, once the correction factor is calculated, adjusting the gain, constant, and slope of the measured spectrum by the calculated correction factor of the gain, constant, and slope.

Further, the bio-information estimation method may further include, once the measured spectrum is adjusted, measuring bio-information by applying a bio-information measuring model to the adjusted spectrum.

In addition, the bio-information estimation method may further include outputting one or more of the measured spectrum, the measured temperature of the object, the estimated bio-information, and warning information generated in response to the estimated bio-information.

According to an aspect of another exemplary embodiment, there is provided a bio-information measuring apparatus, including: a spectrum measurer configured to measure a spectrum of light reflected from an object; a temperature measurer configured to measure temperature of the object while the spectrum measurer measures the spectrum of light reflected from the object; and a processor configured to calculate a spectrum correction factor, including one or more of a correction factor of a gain, a constant, and a slope, based on the measured temperature of the object, to adjust either one of the measured spectrum and a reference spectrum by using the calculated correction factor, and to estimate bio-information based on the adjusted spectrum and the unadjusted one of the measured spectrum and the reference spectrum.

Once temperature is measured by the temperature measurer, the processor may calculate the correction factor by inputting the measured temperature into a correction factor calculation formula.

Further, the bio-information measuring apparatus may further include an output part configured to output one or more of the measured spectrum, the measured temperature of the object, the estimated bio-information, and warning information generated in response to the estimated bio-information.

In addition, the bio-information measuring apparatus may further include a storage part configured to store one or more of the measured spectrum, the measured temperature of the object, the estimated bio-information, warning information generated in response to the estimated bio-information, and information about the reference spectrum.

Moreover, the bio-information measuring apparatus may further include a communicator configured to receive the reference spectrum from an external device.

The reference spectrum may be a spectrum measured at a reference temperature from a standard solution including a component related to the bio-information.

BRIEF DESCRIPTION OF THE DRAWINGS

These and/or other exemplary aspects and advantages will become apparent and more readily appreciated from the following description of exemplary embodiments, taken in conjunction with the accompanying drawings in which.

Figure 1:
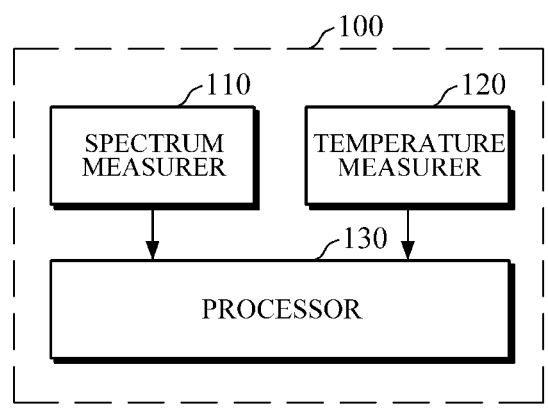
FIG. 1 is a block diagram illustrating a bio-information estimation apparatus according to an exemplary embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Advantages and features of exemplary embodiments will be more clearly understood from the following detailed description, with reference to the accompanying drawings.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as "part", "unit," or "module," etc., should be understood as a unit that performs at least one function or operation and that may be embodied as hardware, software, or a combination thereof.

Figure 2:
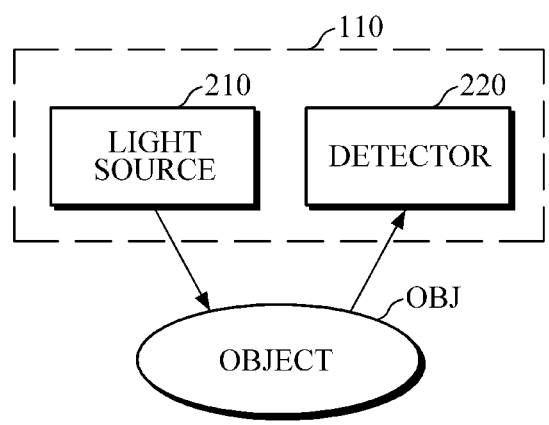
FIG. 2 is a block diagram illustrating an example of a spectrum measurer of the bio-information estimation apparatus of FIG. 1.

FIG. 1 is a block diagram illustrating a bio-information estimation apparatus according to an exemplary embodiment. FIG. 2 is a block diagram illustrating a spectrum measurer of the bio-information estimation apparatus of FIG. 1.

Figure 12:
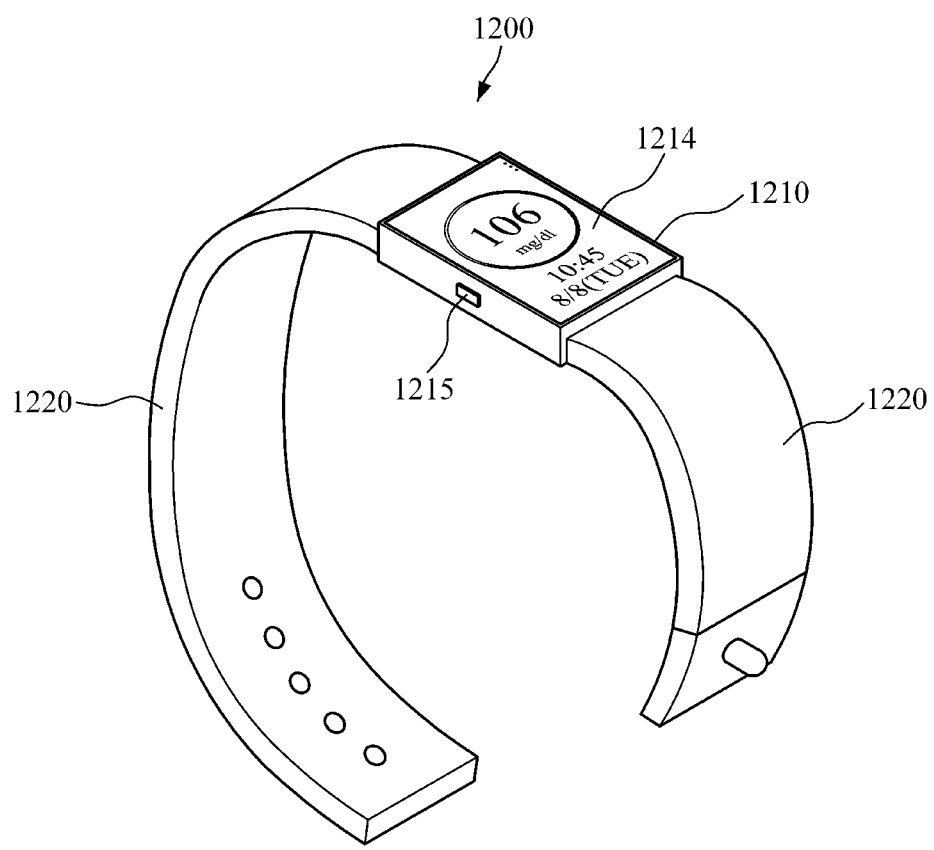
FIG. 12 is a diagram illustrating a wearable device according to an exemplary embodiment.

The bio-information estimation apparatus 100 according to an exemplary embodiment may be manufactured as a watch-type wearable device illustrated in FIG. 12. However, the bio-information estimation apparatus 800 is not limited thereto, and may be not only a bracelet-type wearable device, a wristband-type wearable device, a ring-type wearable device, a glasses-type wearable device, a hairband-type wearable device and the like, but may also be embedded in a portable device, such as a smartphone or a tablet PC, and may be modified to have any of various sizes or shapes according to a desired measurement purpose or a place of use of the bio-information.

Referring to FIG. 1, the bio-information estimation apparatus 100 includes a spectrum measurer 110, a temperature measurer 120, and a processor 130.

The spectrum measurer 110 may measure a spectrum for obtaining bio-information from an object. For example, the spectrum measurer 110 may use infrared spectroscopy or Raman spectroscopy, but is not limited thereto.

The spectrum measurer 110 operates according to a control signal output by the processor 120. Upon receiving the control signal, the spectrum measurer 110 may emit light onto an object, and may measure a spectrum by detecting light emanating from the object. The object may be contacted by the spectrum measurer 110 and may be is a region of a user's skin, which may be the back of a hand or the wrist through which venous blood passes, or a surface of the wrist through which capillary blood passes, but is not limited thereto.

Referring to FIG. 2, the spectrum measurer 110 includes a light source 210 which emits light onto an object OBJ, and a detector 220 which detects light reflected from the object OBJ, after having been emitted from the light source 210. The light source 110 may emit Near Infrared Ray (NIR) or Mid Infrared Ray (MIR), and may emit laser light when using Raman spectroscopy. The light source 111 may be a light emitting diode (LED), a laser diode, or the like, but is not limited thereto. The light source 110 may be a single light source, or an array of a plurality of light sources. The light source 110 may et it light of any of various wavelength bands by using various methods, such as a method of adjusting the temperature of a light source, as would be understood by one of skill in the art.

The detector 220 may be a photo diode, a photo transistor (PTr), a charge-coupled device (CCD), or the like. The detector 220 may be a single detector or an array of a plurality of detectors.

The temperature measurer 120 may measure the temperature of the spectrum while the spectrum measurer 110 measures the spectrum of the light reflected from the object, for example, a temperature of the object at the time of measuring the spectrum. When the spectrum measurer 110 is adhered to the object to measure the spectrum from the object, the temperature measurer 120 may be disposed in the same physical unit as the spectrum measurer 110 at a position adjacent thereto, so that the temperature measurer 120 may also be adhered to the object along with the spectrum measurer 110. However, the temperature measurer 120 is not limited thereto, and may be provided as a hardware device separately from the spectrum measurer 110 or the processor 130.

The processor 130 may receive a user command, such as a request for estimating bio-information, from a user, and may generate a control signal corresponding to the received user command to control the spectrum measurer 110 and various other parts not shown in the drawings. The processor 130 may receive, from the spectrum measurer 110, spectrum information measured from the light reflected by the object, and may receive temperature information of the object at the time of measuring the spectrum from the temperature measurer 120. The processor 130, the spectrum measurer 110, and the temperature measurer 120 may be electrically connected with each other.

In a case in which the temperature measurer 120 fails to measure the temperature, and thus, the temperature information is not received for a predetermined period of time, or in a case in which the received temperature information falls outside a predetermined threshold value, the processor 130 may generate alarm information, and may control an output module to provide the generated alarm information to a user.

Upon receiving the spectrum information and temperature information, the processor 130 may estimate the bio-information by using the received spectrum information and temperature information. The bio-information may include one or more of blood glucose, cholesterol, triglyceride, protein, alcohol, and uric acid. However, the bio-information is not limited thereto, but the description below will be made based on an example of blood glucose for convenience of explanation.

Upon estimating the bio-information, the processor 130 may control an output module to t an estimation result of the bio-information, the spectrum used for the estimation of bio-information, a correction factor, warning information generated in response to the existence of an abnormality in the estimation result of bio-information, and the like.

Figure 3:
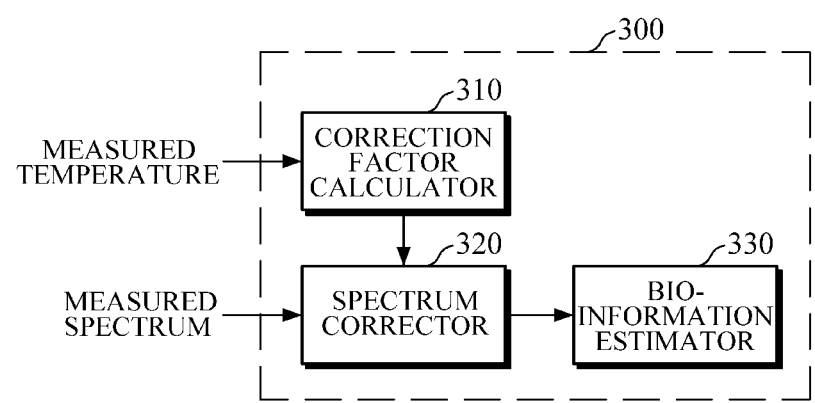
FIG. 3 is a block diagram illustrating an example of a processor of the bio-information estimation apparatus of FIG. 1.

FIG. 3 is a block diagram illustrating an example of a processor of the bio-information estimation apparatus of FIG. 1. FIGS. 4A to 4D are diagrams explaining a spectrum change according to a temperature change according to an exemplary embodiment.

Figure 4A:
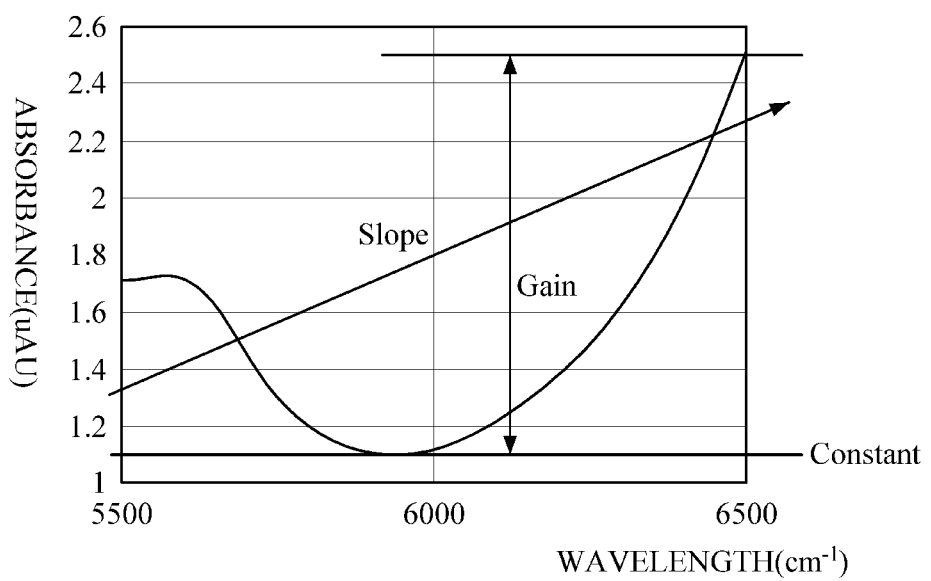
FIGS. 4A to 4D are diagrams explaining a spectrum change according to a temperature change according to an exemplary embodiment.
Figure 4B:
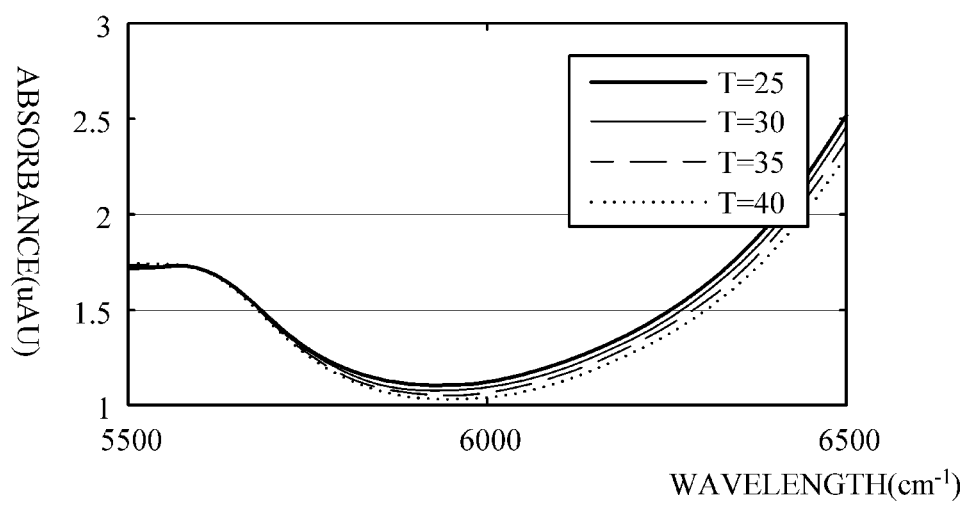
Figure 4C:
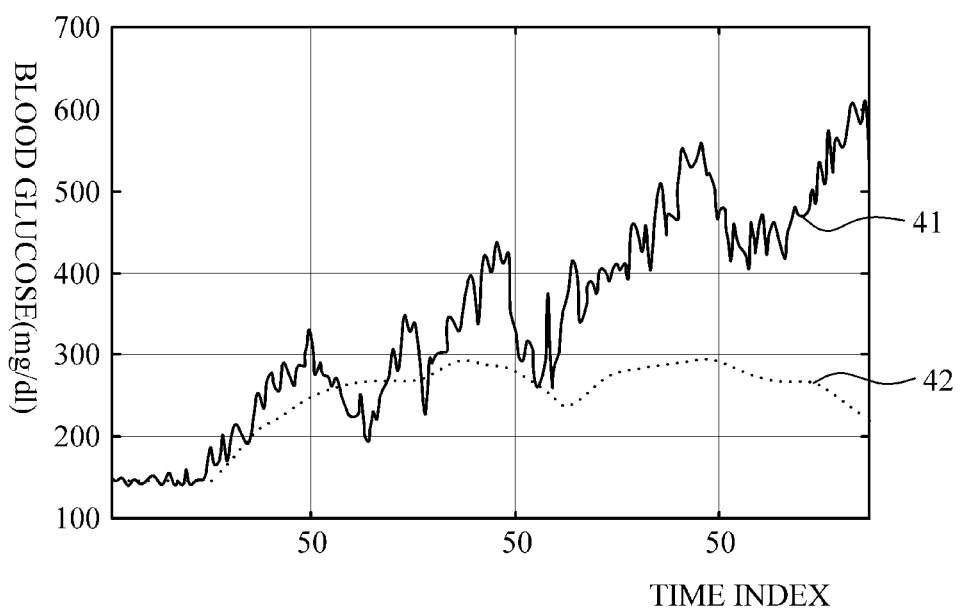
Figure 4D:
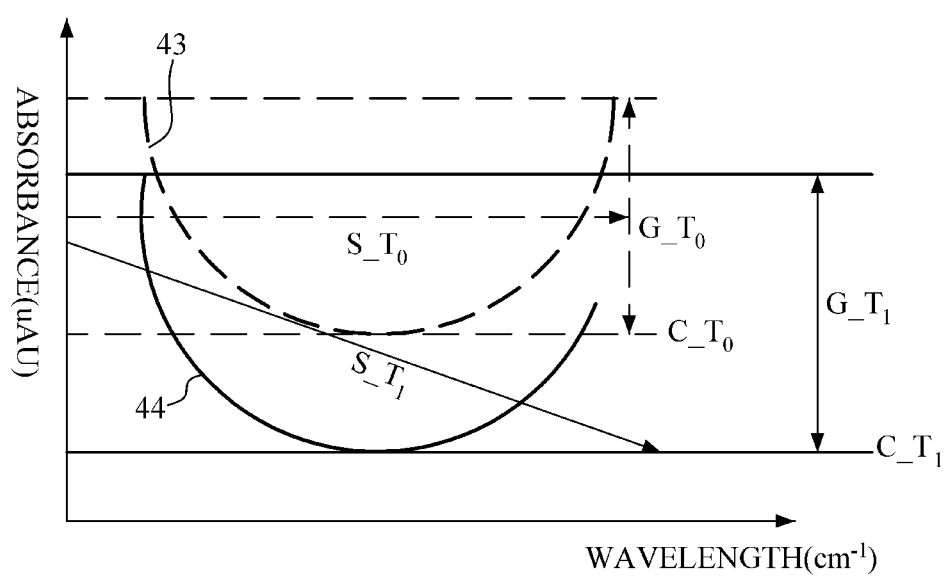

Referring to FIGS. 3 to 4D, an example of the processor 130 of the bio-information estimation apparatus FIG. 1 will be described. Referring to FIG. 3, the processor 300 includes a correction factor calculator 310, a spectrum corrector 320, and a bio-information estimator 330.

FIG. 4A illustrates a spectrum measured at a temperature of 25° C., and a gain, a constant, and a slope of the spectrum. Here, the gain may indicate a difference between a minimum absorbance and a maximum absorbance over the entire wavelength band (e.g., 5500 $cm^{-1}$ to 6500 $cm^{-1}$) of the detected spectrum. The constant may indicate a minimum absorbance over the entire wavelength band (e.g., 5500 $cm^{-1}$ to 6500 $cm^{-1}$) of the detected spectrum. However, the gain and the constant are not limited thereto, and may be defined as an average value, a mean value, or the like between the minimum absorbance and the maximum absorbance. The slope may indicate a slope of a spectrum waveform over the entire wavelength band (e.g., 5500 $cm^{-1}$~6500 $cm^{-1}$) of the detected spectrum. However, the slope is not limited thereto, and may be a slope of any of various sections, such as a section in which the absorbance is increased, for example a section between a minimum point (e.g., 5900 $cm^{-1}$) and a maximum point (e.g., 6500 $cm^{-1}$) immediately after the minimum point, or a section in which the absorbance is decreased, for example a section between the minimum point (e.g., 5900 $cm^{-1}$) and a maximum point (e.g., 5600 $cm^{-1}$) immediately before the minimum point, or the like.

FIG. 4B illustrates a spectrum change according to a change of the measured temperature.

When bio-information is measured over a long period of time, heat may be generated by the light source or by body temperature, or there may be a change in external temperature, thereby effecting the object, the detector, or the like. When the temperature of the object changes, the gain, constant, and slope of a spectrum measured at the changed temperature may also change as compared to a spectrum measured at a reference temperature. For example, referring to FIG. 4B, as the temperature gradually changes from 25° C. to 40° C., the gain, constant, and slope of the spectrum show a tendency to gradually decrease.

FIG. 4C is a graph showing comparison of a result of long-term estimation 41 of blood glucose by using a related art blood glucose method and an actual measurement result 42 of blood glucose. As illustrated in FIG. 4C, in the case in which blood glucose is measured for a long period of time, the gain, constant, and slope of the measured spectrum vary due to a temperature change of the object and the like, such that when bio-information, e.g., blood glucose, is estimated by using a bio-information model built based on the reference temperature, the accuracy of estimation may be reduced.

The correction factor calculator 310 may calculate a correction factor for adjusting a spectrum based on the temperature of the measured spectrum, so that the variance of the spectrum change due to temperature changes may be taken into account when estimating bio-information.

For example, referring to FIG. 4D, in the case in which a spectrum is measured with a temperature of the object at 30° C., a spectrum 44 measured at 30° C. has a gain ($G\_T_1$), a constant ($S\_T_1$), and a slope ($S\_T_1$). Assuming that a spectrum 43 measured at a reference temperature of, for example, 25° C. has a gain (G_T$_0$), a constant (S_T$_0$), and a slope (S_T$_0$), it can be seen that the constant (S_T$_1$) and the slope (S_T$_1$) of the measured spectrum 44 are decreased as compared to the reference temperature, and the gain (G_T$_1$) of the measured spectrum 44 is increased.

In order to change the spectrum 44 measured at the changed temperature (e.g., 30° C.) to the spectrum measured at the reference temperature (e.g., 25° C.), the correction factor calculator 310 may calculate a correction factor for the gain (G_T$_1$), the constant (S_T$_1$), and the slope (S_T$_1$) of the measured spectrum 44.

For example, the correction factor calculator 310 may calculate a correction factor by inputting the measured temperature into each correction factor calculation formula such as the following Equation 1. The correction factor calculation formula 310 is not necessarily in a linear function form such as Equation 1, and may be in a table form in which a correction factor is matched with the measured temperature or with each temperature section. As will be described later, each correction factor calculation formula may be pre-obtained based on a result of correlation between a spectrum, which is measured from the object or a standard solution at the reference temperature (e.g., 25° C.), and a spectrum measured according to a temperature change (e.g., 30° C., 35° C., 40° C., etc.). The standard solution may be a solution including a component (e.g., glucose) related to bio-information to be estimated, or a glucose serum solution which is similar to a skin tissue of the human body.

$$y_g = a_g T + b_g$$

$$y_s = a_s T + b_s$$

$$y_c = a_c T + b_c \quad \text{[Equation 1]}$$

Herein, $y_g$, $y_s$ and $y_c$ are calculation results of the gain, slope, and constant respectively; $a_g$, $b_g$, $a_s$, $b_s$, $a_c$, and $b_c$ are constants pre-calculated through pre-processing; and T is the temperature measured at the time of measuring a spectrum.

Once the correction factor is calculated, the spectrum corrector 320 may correct the measured spectrum to correspond to a spectrum measured at the reference temperature by adjusting the gain, constant, slope, and the like of the measured spectrum by using the calculated correction factor.

For example, once the correction factor is calculated, the spectrum corrector 320 may correct the measured spectrum by increasing or decreasing the gain, constant, and slope of the measured spectrum by the calculated correction factor for the gain, constant, and slope in consideration of the tendency of the spectrum to change according to a change in the measured temperature as compared to the reference temperature. According to an increasing or decreasing of the temperature, each change in the gain, constant, and slope of the spectrum may be predefined through preprocessing based on various types of bio-information, an object to be examined, and the like.

Once the measured spectrum is adjusted, the bio-information estimator 330 may estimate bio-information by using the adjusted spectrum. For example, the bio-information estimator 330 may estimate the bio-information by applying a pre-generated bio-information estimation model. The bio-information estimation model may be a linear function equation which is pre-generated by analyzing a correlation between a plurality of spectrums measured at the reference temperature and an actual bio-information estimation value, e.g., an actual blood glucose value measured in an invasive manner.

Figure 5:
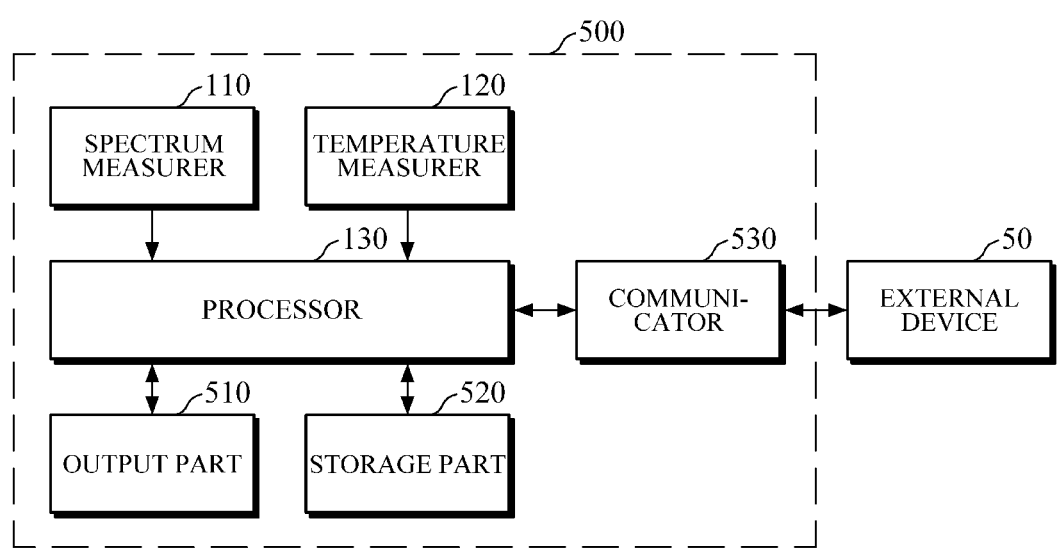
FIG. 5 is a block diagram illustrating a bio-information estimation apparatus according to another exemplary embodiment.
Figure 6:
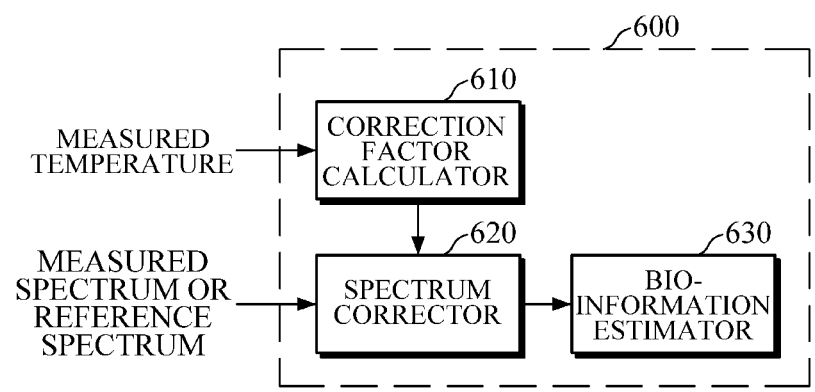
FIG. 6 is a block diagram illustrating an example of a processor of the bio-information estimation apparatus of FIG. 5.

FIG. 5 is a block diagram illustrating a bio-information estimation apparatus according to another exemplary embodiment. FIG. 6 is a block diagram illustrating an example of a processor of the bio-information estimation apparatus of FIG. 5. Referring to FIGS. 5 and 6, exemplary embodiments of the bio-information estimation apparatus will be described below.

The bio-information estimation apparatus 500 according to an exemplary embodiment may be manufactured as a watch-type wearable device illustrated in FIG. 12. However, the bio-information estimation apparatus 800 is not limited thereto, and may be not only a bracelet-type wearable device, a wristband-type wearable device, a ring-type wearable device, a glasses-type wearable device, a hairband-type wearable device and the like, but may alternately be embedded in a portable device, such as a smartphone or a tablet PC, and may be modified into any of various sizes or shapes according to a desired purpose or place of use of the bio-information.

Referring to FIG. 5, the bio-information estimation apparatus 500 includes a spectrum measurer 110, a temperature measurer 120, a processor 130, an output pat 510, a storage part 520, and a communicator 530. The spectrum measurer 110, the temperature measurer 120, and the processor 130 basically perform the same functions as those described above with reference to FIGS. 1 to 3, such that descriptions below will be made based on details that do not overlap.

Referring to FIG. 6, the processor 600 according to the exemplary embodiment of the processor 130 of FIG. 5 includes a correction factor calculator 610, a spectrum corrector 620, and a bio-information measurer 630.

Once a spectrum and temperature at the time of measuring the spectrum are obtained, the correction factor calculator 610 may calculate a correction factor for adjusting the spectrum based on temperature of the object at the time of measuring the spectrum. As described above, the correction factor calculator 610 may calculate each correction factor by inputting the measured temperature into each correction factor calculation formula.

Upon calculating the correction factor, the spectrum corrector 620 may make adjustments by using the calculated correction factor. The reference spectrum may be a spectrum measured at the reference temperature (e.g., 25° C.) from the above-described standard solution.

For example, upon calculating the correction factor, the spectrum corrector 620 may modify the measured spectrum to correspond to a spectrum measured at the reference temperature by adjusting the gain, constant, slope, and the like of the measured spectrum. Alternatively, by adjusting the gain, constant, slope, and the like of the reference spectrum by using the calculated correction factor, the spectrum corrector 620 may adjust the reference spectrum measured at the reference temperature (e.g., 30° C.) to correspond to a spectrum measured at the temperature (e.g., 30° C.) which is the temperature at the time that the reference spectrum is measured by the spectrum measurer 110.

Further, the spectrum corrector 620 may determine whether to modify the reference spectrum or the measured spectrum with reference to the storage part 520. In the storage part 520, it may be preset to correct the measured spectrum, and a user may change the setting to the reference spectrum in consideration of their circumstances.

Once the measured spectrum or the reference spectrum is adjusted, the bio-information estimator 630 may estimate bio-information by using the adjusted spectrum and the remaining unadjusted spectrum. The bio-information estimator 630 may estimate bio-information from the measured spectrum and the reference spectrum by applying the pre-generated bio-information estimation model. In order to remove a noise of the measured spectrum which is measured by the spectrum measurer 110, the bio-information estimator 630 may estimate bio-information by, for example, using a result obtained by removing a background spectrum measured in an empty stomach state, from the measured spectrum and by using the reference spectrum.

For example, assuming that five background spectrums $S_f = \{S_{f1}, S_{f2}, S_{f3}, S_{f4}, S_{f5}\}$ are obtained at regular time intervals in an empty stomach state, and the measured spectrum $S_{pt}$ is measured at a specific time t, the bio-information estimator 630 may estimate blood glucose by using the following Equations 2 and 3. However, the following Equations are merely exemplary for estimation of blood glucose, and the estimation of bio-information is not limited thereto and may use any of various algorithms using the reference spectrum and the measured spectrum for estimation of bio-information. In the following Equations, either one of the measured spectrum $S_{pt}$ and the reference spectrum $\varepsilon_g$ is a spectrum adjusted by the spectrum corrector 620, but they will be referred to as the measured spectrum and the reference spectrum for convenience of explanation.

$$S_{pt} = b_1 BS_1 + b_2 BS_2 + b_3 BS_3 + b_4 BS_4 - b_5 BS_5 + \varepsilon_g L_t \Delta C_t \quad \text{[Equation 2]}$$

$$C_t = \Delta C_t + C_0 \quad \text{[Equation 3]}$$

Referring to FIG. 2, the bio-information estimator 630 extracts background signals $BS = \{BS_1, BS_2, BS_3, BS_4, BS_5\}$ from a background spectrum $S_f$ by using principal component analysis and the like, and may estimate a blood glucose signal $\varepsilon_g L_t \Delta C_t$, by subtracting the extracted background signal from the spectrum $S_{pt}$ measured at the specific time t. Upon extracting the blood glucose signal $\varepsilon_g L_t \Delta C_t$, the bio-information estimator 630 may calculate a blood glucose variation $\Delta C_t$ at a specific time t by using the pre-stored reference spectrum $\varepsilon_g$ and light traveling path $L_t$. In the estimation of blood glucose, it is assumed that a blood glucose level $C_0$ on an empty stomach state is constant, such that upon calculating the blood glucose variation $\Delta C_t$, the bio-information estimator 630 may estimate blood glucose $C_t$ at the time t by inputting the calculated blood glucose variation $\Delta C_t$ into Equation 3. Here, b1, b2, b3, b4, and b5 indicate coefficients of background signals $BS_1$, $BS_2$, $BS_3$, $BS_4$, and $BS_5$ calculate by using a least square method and the like.

Referring back to FIG. 5, the output part 510 may display any of various types of information, processed by the spectrum measurer 110, the temperature measurer 120, and the processor 130, on a display, or may provide the information to a user by a non-visual method such as voice, vibration, and the like.

For example, the output part 510 may display the spectrum measured by the spectrum measurer 110 and the temperature of the spectrum that is measured by the temperature measurer 120 on a display. Further, the output part 510 may display an estimation result of the bio-information estimated by the processor 130 on a display. The output part 510 may display the estimation result of bio-information in a predetermined area of the display, and may display, by a user's input or automatically, the spectrum, the measured temperature, the calculated correction factor, the spectrum before adjustment, and the like, which are used for estimation of bio-information, in other area of the display by using various visual methods. In addition, the output part 510 may output warning information or additional information related to a user's health state according to the estimation result of bio-information. For example, in the case in which an estimated blood glucose level falls outside a normal range, the output part 510 may display the information in red on a display.

In another example, in the case in which the temperature measurer 120 fails to measure temperature, or in the case in which the measured temperature falls outside a predetermined threshold value, the output part 510 may output alarm information by the control of the processor 130. In the case in which temperature information is not received from the temperature measurer 120 for a predetermined period of time, the processor 130 determines whether the measured temperature is normal temperature within a predetermined threshold value; and upon determination, if the measured temperature is not normal temperature, the processor 130 may control the output part 510 to output alarm information.

The storage part 520 may store any of various types of reference information useful for estimation of bio-information, or may store a processing result of the spectrum measurer 110, the temperature measurer 120, and the processor 130. The reference information may include user feature information, which is related to a user's age, gender, health state, and the like, a correction factor calculation formula, a bio-information estimation model, and the like.

The storage part 520 may include at least one storage medium comprising a flash memory memory, a hard disk memory, a multimedia card micro memory, a card memory (e.g., a Secure Digital (SD) memory, an eXtreme Digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, an optical disk, or the like, but is not limited thereto.

The communicator 530 may be connected with an external device by accessing a communication network using a communication technique by the control of the processor 130. The communication technique may include Bluetooth, Bluetooth Low Energy (BLE), Near Field Communication (NFC), WLAN (WIFI), Zigbee, Infrared Data Association (IrDA), Wi-Fi Direct (WFD), Ultra-Wideband (UWB), Ant+, WIFI, and mobile, but is not limited thereto.

For example, the communicator 530 may receive, from an external device 50, the reference information including the correction factor calculation formula, the bio-information estimation model, the reference spectrum, and the like. The external device 50 may be a bio-information measuring apparatus utilizing an invasive/non-invasive manner, or an apparatus which measures a reference spectrum from a standard solution and generates a correction factor calculation formula. In addition, the external device 50 may be a device having a function of calculating a correction factor formula or a function of generating a bio-information estimation model, or may be a device which may receive a correction factor calculation formula or a bio-information estimation model from a user.

Alternatively, the communicator 530 may transmit, to the external device 50, the measured spectrum, the measured temperature, the estimation result information, and the like, so as to provide a monitoring result of a user's health state, an estimation result of bio-information, detailed analysis information, and the like to a user. The external device 50 may include an information processing device, such as a mobile terminal, a tablet PC, a desktop computer, a laptop computer, a server device, or the like, which has a relatively high computing performance.

Figure 7:
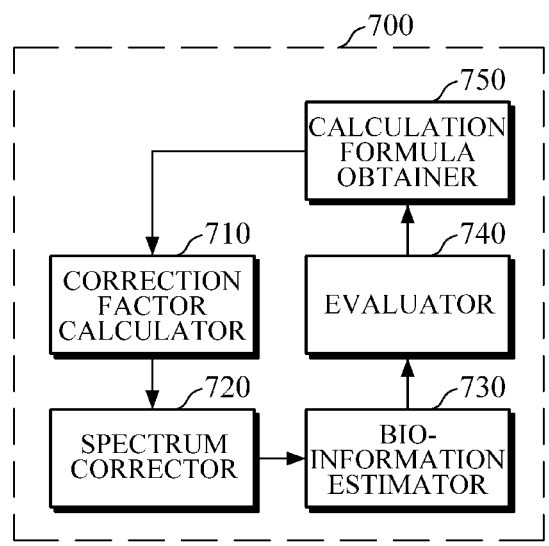
FIG. 7 is a block diagram illustrating an example of a processor of the bio-information estimation apparatus of FIG. 1 or FIG. 5.
Figure 8A:
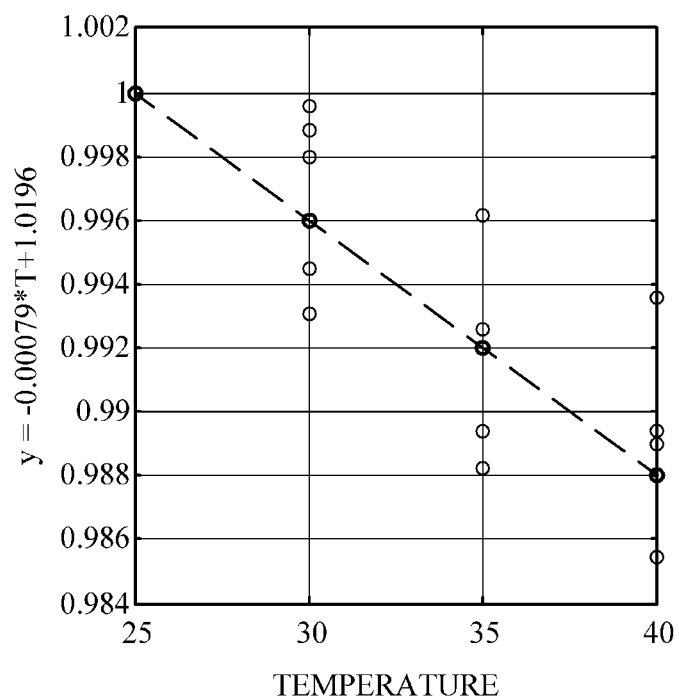
FIGS. 8A to 8C are diagrams explaining generation of a correction factor calculation formula according to an exemplary embodiment.
Figure 8B:
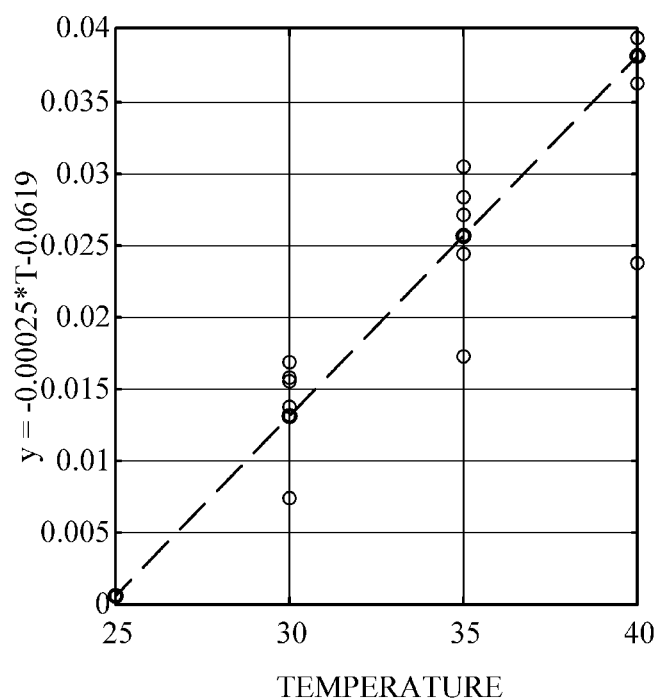
Figure 8C:
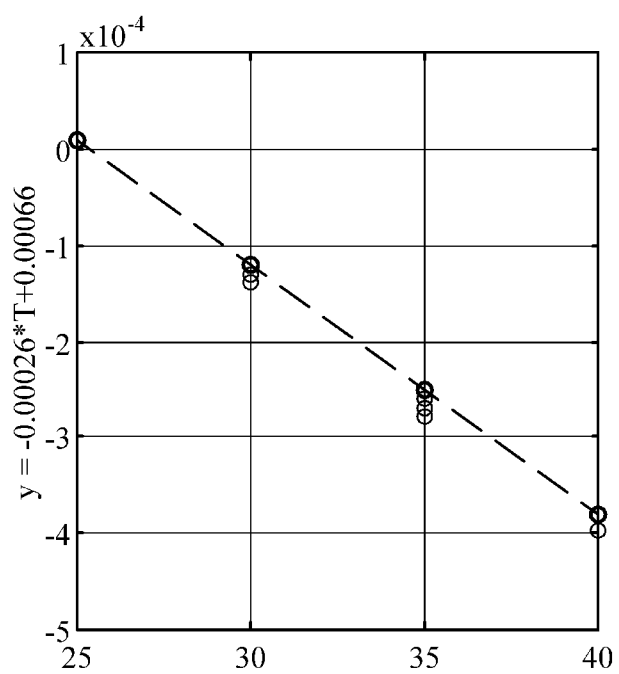

FIG. 7 is a block diagram illustrating an example of the processor 130 of FIG. 1 or FIG. 5. FIGS. 8A to 8C are diagrams explaining examples of generating a correction factor calculation formula.

Referring to FIG. 7, the processor 700 according to the exemplary embodiment of the processor 130 of FIG. 5 includes a correction factor calculator 710, a spectrum corrector 720, a bio-information estimator 730, an evaluator 740, and a calculation formula obtainer 750.

Once a spectrum and temperature at the time of measuring the spectrum are obtained, the correction factor calculator 710 may calculate a correction factor for adjusting the spectrum based on temperature of the measured spectrum. As described above, the correction factor calculator 710 may calculate each correction factor by inputting the measured temperature into each correction factor calculation formula.

Upon calculating the correction factor, the spectrum corrector 720 may correct the measured spectrum or the reference spectrum by using the calculated correction factor. For example, as illustrated in FIG. 1, in the case in which the bio-information estimator 630 estimates bio-information by using only the measured spectrum without using the reference spectrum, the spectrum corrector 720 may correct the measured spectrum. In another example, as illustrated in FIG. 5, even in the case in which the bio-information estimator 630 estimates bio-information by using the measured spectrum along with the reference spectrum, the spectrum corrector 720 may also correct the measured spectrum if the storage part 520 is set to correct the measured spectrum.

According to a pre-generated bio-information estimation model, the bio-information estimator 630 may estimate bio-information by using only the measured spectrum as illustrated in FIG. 1, or by using the measured spectrum along with the reference spectrum as illustrated in FIG. 5. As described above, in order to remove a noise of the measured spectrum, a background spectrum measured in an empty stomach state may also be used.

An evaluator 740 may determine whether to re-generate a correction factor calculation formula by considering the existence of an abnormality in the estimation result of bio-information, user input information, a predetermined bio-information generating period, and the like. For example, upon receiving a request for re-generating a correction factor calculation formula from a user, the evaluator 740 may determine to re-generate the correction factor calculation formula. Alternatively, the evaluator 740 may check, with reference to the storage part 520, whether the bio-information re-generating period is set; and upon checking, if it is the bio-information re-generating period, the evaluator 740 may determine to re-generate the correction factor calculation formula. Alternatively, the evaluator 740 may determine to re-generate the correction factor calculation formula based on an estimation history of bio-information. For example, in the case in which the number of bio-information estimation values during a specific period which fall outside a predetermined range exceeds a predetermined threshold value, the evaluator 740 may determine to re-generate a correction factor calculator formula. The predetermined range refers to a range of bio-information estimation values set for each user according to user feature information, for example, a user's health state including whether the user has diabetes and the like, but is not limited thereto.

Once the evaluator 740 determines to re-generate the correction factor calculation formula, the calculation formula obtainer 750 may collect a plurality of spectrums and temperature information obtained from an object at various temperatures including the reference temperature, and may re-generate the correction factor calculation formula by analyzing correlations between various temperature changes spectrums by using the collected learning data through an algorithm, such as regression analysis, machine learning, and the like.

FIG. 8A illustrates a graph showing gains of a plurality of spectrums measured at 25° C., 30° C., 35° C., and 40° C. FIG. 8B is a graph showing constants of the plurality of spectrums measured at 25° C., 30° C., 35° C., and 40° C. FIG. 8C is a graph showing slopes of the plurality of spectrums measured at 25° C., 30° C., 35° C., and 40° C. By graphically displaying the correction factors of the plurality of spectrums for each temperature, it can be seen that there is a correlation between the temperature and each correction factor, which may be represented by a linear function equation. The linear function equation obtained in this manner may be determined to be a correction factor calculation formula of each correction factor.

In another example, the calculation formula obtainer 750 may control the communicator 530 to transmit a request for a new correction factor calculation formula to an external device 50, and may receive the requested new correction factor calculation formula from the external device 50. The external device may be a device for calculating a correction factor calculation formula based on the spectrum measured from the above-described standard solution at various temperatures including the reference temperature.

Figure 9:
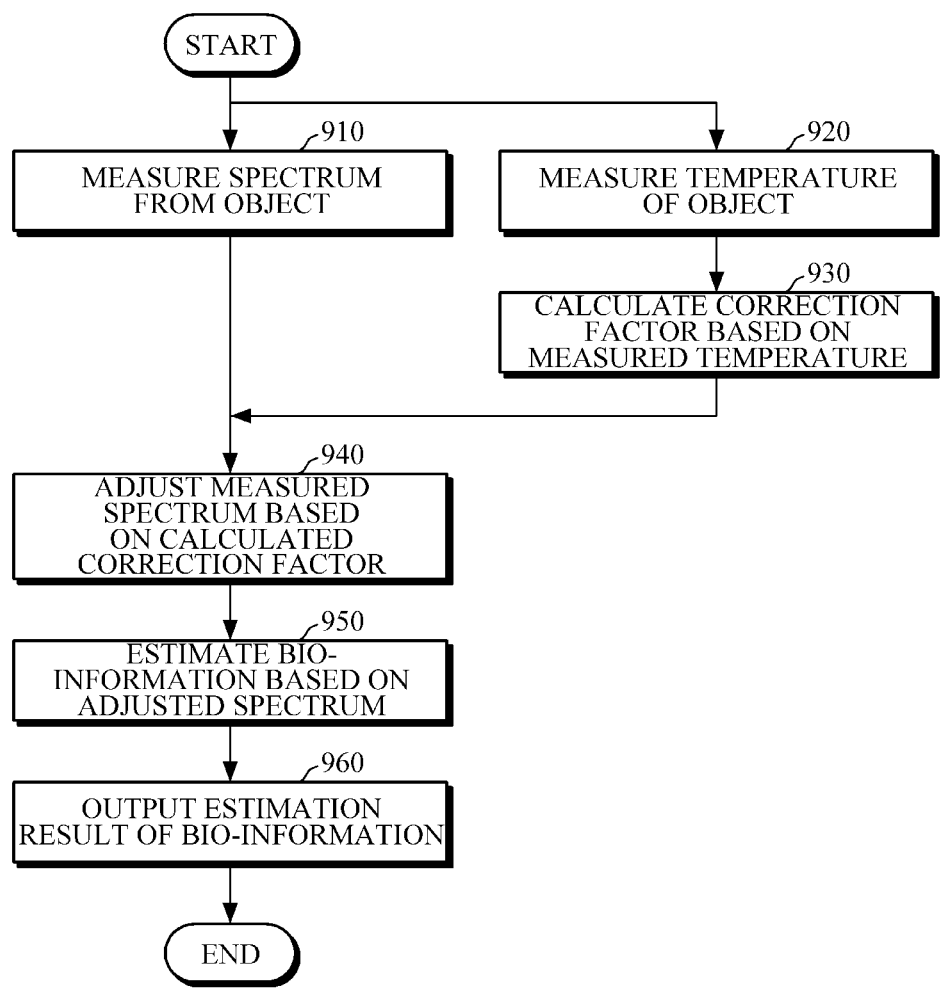
FIG. 9 is a flowchart illustrating a bio-information estimation method according to an exemplary embodiment.

FIG. 9 is a flowchart illustrating an example of a bio-information estimation method. FIG. 9 is an example of a bio-information estimation method performed by the bio-information estimation apparatus 100 of FIG. 1.

Upon receiving a request for estimating bio-information, the bio-information estimation apparatus 100 may measure a spectrum of light reflected from an object in 910. The bio-information estimation apparatus 100 may obtain a spectrum by controlling a light source to emit light onto an object, and by detecting light reflected from the object.

Further, while measuring the spectrum of light reflected from the object, the bio-information estimation apparatus 100 may measure a temperature at the time of measuring the spectrum in 920. In the case in which the spectrum is measured for a long period of time, temperature of the object, with respect to which the spectrum is measured, may change according to a change of the temperature of a light source or the user's body or according to a change of the temperature of an external environment. Such temperature changes may distort the measured spectrum as compared to a spectrum measured at the reference temperature. In response to a failure to measure temperature for a predetermined period of time, or in response to the measured temperature falling outside a predetermined threshold value, the bio-information estimation apparatus 100 may generate alarm information and ay output the generated alarm information to a user.

Then, the bio-information estimation apparatus 100 may calculate a correction factor based on the measured temperature in 930. The correction factor of the spectrum may include a gain indicative of the amplitude of the spectrum, a constant indicative of an offset of the spectrum, and a slope indicative of a slope of the spectrum. For example, the bio-information estimation apparatus 100 may calculate a correction factor to correct the measured spectrum to correspond to a spectrum measured at the reference temperature by inputting the measured temperature into a pre-defined correction factor calculation formula.

Subsequently, upon calculating the correction factor in 930, the bio-information estimation apparatus 100 may convert the measured spectrum, which is measured at the measured temperature, to correspond to the spectrum measured at the reference temperature by adjusting the measured spectrum based on the calculated correction factor in 940.

Next, the bio-information estimation apparatus 100 may estimate bio-information based on the adjusted spectrum in 950. The bio-information estimation apparatus 100 may estimate bio-information, such as blood glucose, from the adjusted spectrum by applying a pre-generated bio-information estimation model.

Then, the bio-information estimation apparatus 100 may output various types of information, including an estimation result of bio-information to a display or may provide the information in the form of a voice signal to a user in 960. The bio-information estimation apparatus 100 may display, on a display, detailed information including the spectrum (e.g., the measured spectrum and the adjusted spectrum), the measured temperature, the calculated correction factor, warning information, and the like, which are used for estimating bio-information, along with the estimation result of bio-information. Alternatively, the bio-information estimation apparatus 100 may display an estimation history of bio-information during a specific period in a predetermined area of the display; and in the case in which a user selects an estimation result of bio-information at a specific time in the predetermined display area, the bio-information estimation apparatus 100 may display various types of detailed information, used in the selected estimation result of bio-information, in response to the user selection.

Figure 10:
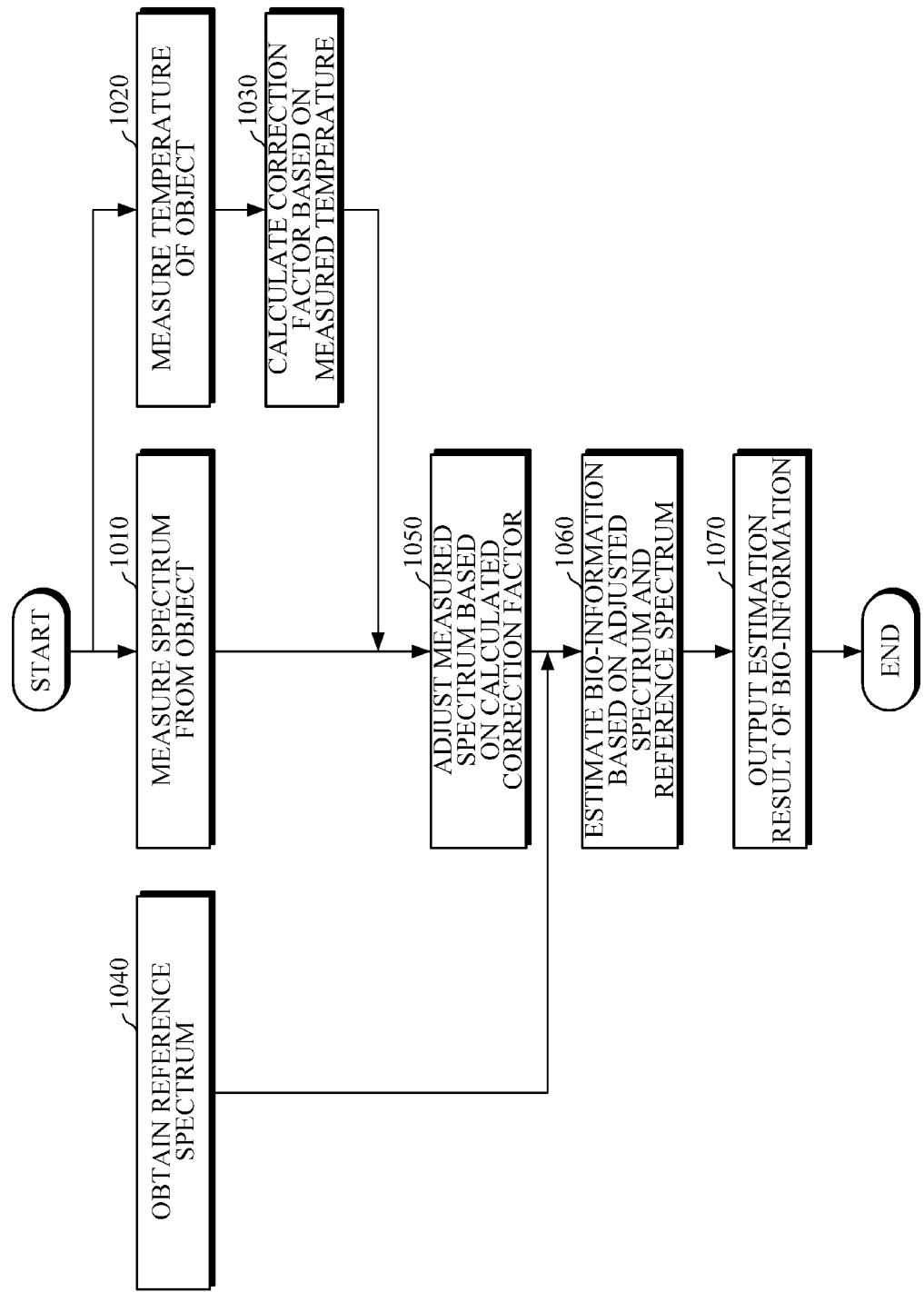
FIG. 10 is a flowchart illustrating a bio-information estimation method according to another exemplary embodiment.

FIG. 10 is a flowchart illustrating a bio-information estimation method according to another exemplary embodiment. FIG. 10 is an example of a bio-information estimation method performed by the bio-information estimation apparatus 500 of FIG. 5.

Upon receiving a request for estimating bio-information, the bio-information estimation apparatus 500 may measure a spectrum of light reflected from an object in 1010. The bio-information estimation apparatus 500 may obtain the spectrum by driving a light source to emit light onto the object, and by detecting light reflected from the object.

Further, while measuring the spectrum from the object, the bio-information estimation apparatus 500 may measure the temperature at the time of measuring the spectrum in 1020.

Then, upon completing measurement of the spectrum in 1010, the bio-information estimation apparatus 500 may calculate a correction factor based on the measured temperature in 1030.

The bio-information estimation apparatus 500 may obtain, from a storage module, a reference spectrum pre-stored in the storage module, or may receive the reference spectrum from an external device by controlling a communication module in 1040. The operation 1040 may be performed before or after the operations 1010 to 1030 or may be performed therebetween.

Next, upon calculating the correction factor in 1030, the bio-information estimation apparatus 500 may convert the measured spectrum, which is measured at the measured temperature, to a spectrum measured at the reference temperature by adjusting the measured spectrum based on the calculated correction factor in 1050. For example, by checking whether the measured temperature is increased or decreased as compared to the reference temperature, and by considering a predefined change tendency of the spectrum according to the increase or decrease of the measured temperature, the bio-information estimation apparatus 500 may increase or decrease the gain, constant, and slope of the measured spectrum by the calculated correction factor of the gain, constant, and slope.

Subsequently, the bio-information estimation apparatus 500 may estimate bio-information based on the adjusted spectrum and the reference spectrum in 1060. The bio-information estimation apparatus 500 may estimate bio-information by applying any of various bio-information estimation models, including the above-described Equations 2 and 3, based on the adjusted reference spectrum and the measured spectrum.

Then, the bio-information estimation apparatus 500 may output any of various types of information, including an estimation result of bio-information, to a display or may provide the information in the form of a voice signal to a user in 1070.

Figure 11:
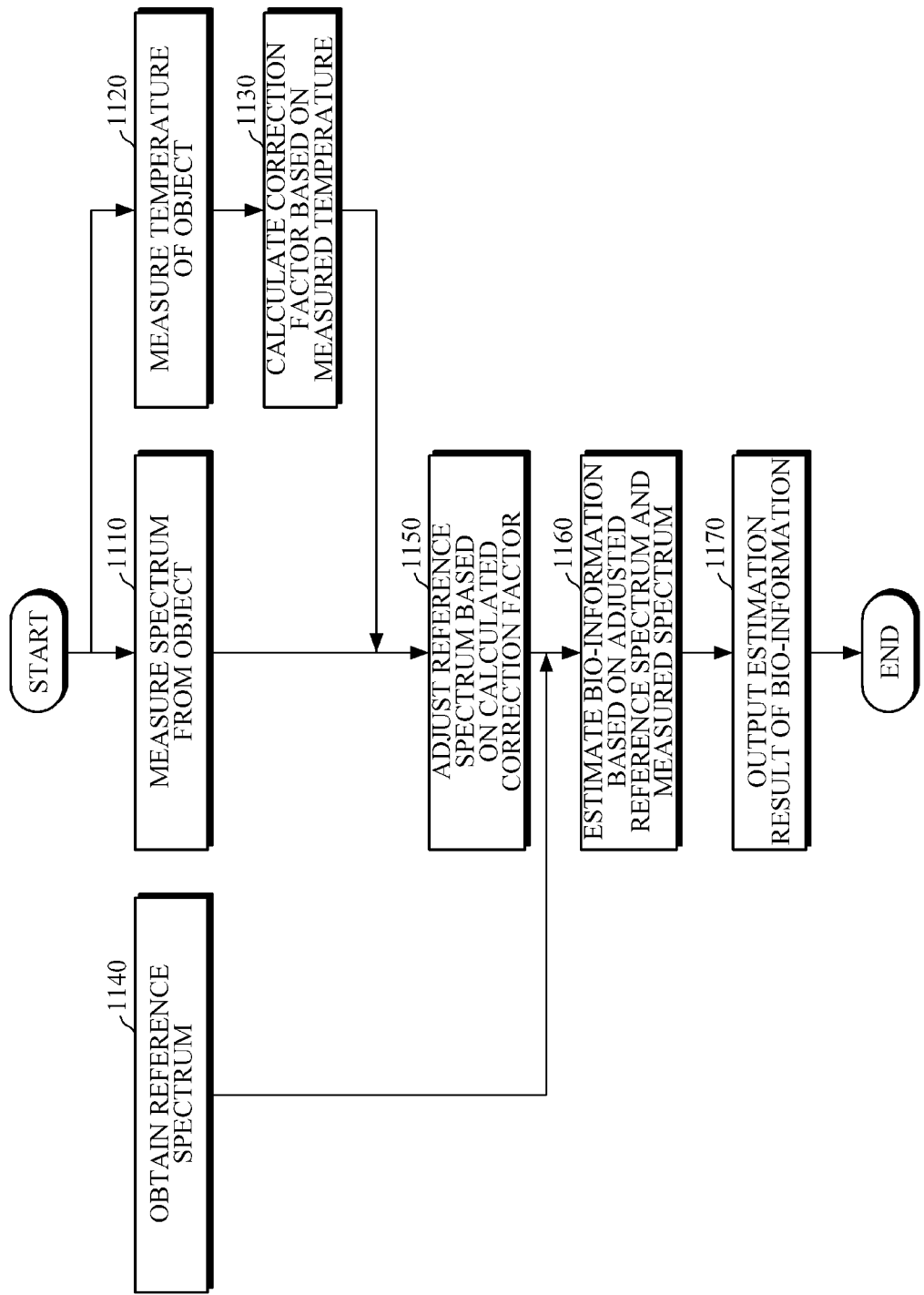
FIG. 11 is a flowchart a bio-information estimation method according to another exemplary embodiment.

FIG. 11 is a flowchart illustrating a bio-information estimation method according to another exemplary embodiment. FIG. 11 is another example of a bio-information estimation method performed by the bio-information estimation apparatus 500 of FIG. 5.

Upon receiving a request for estimating bio-information, the bio-information estimation apparatus 500 may measure a spectrum of light reflected from an object in 1110. The bio-information estimation apparatus 500 may obtain the spectrum by driving a light source to emit light onto the object, and by detecting light reflected from the object.

Further, while measuring the spectrum of light reflected from the object, the bio-information estimation apparatus 500 may measure temperature at the time of measuring the spectrum in 1120.

Then, upon completing measurement of the spectrum in 1110, the bio-information estimation apparatus 500 may calculate a correction factor based on the measured temperature in 1130.

The bio-information estimation apparatus 500 may obtain, from a storage module, a reference spectrum pre-stored in the storage module, or may receive the reference spectrum from an external device by controlling a communication module in 1140. The operation 1140 may be performed before or after the operations 1110 to 1130 or may be performed therebetween.

Based on the calculating of the correction factor in 1130, the bio-information estimation apparatus 500 may convert the reference spectrum, which is measured at the reference temperature, to a spectrum measured at the measured temperature by adjusting the reference spectrum based on the calculated correction factor in 1150.

Thereby, the bio-information estimation apparatus 500 may estimate the bio-information based on the adjusted reference spectrum and the measured spectrum in 1160.

The bio-information estimation apparatus 500 may output various types of information, including the estimation result of bio-information, to a display or may provide the information in the form of a voice signal to a user in 1170.

FIG. 12 is a diagram illustrating an example of a wearable device. FIG. 12 illustrates a smart watch-type wearable device worn on a user's wrist, as an exemplary embodiment of the above-described bio-information estimation apparatuses 100 and 500.

Referring to FIG. 12, the wearable device 1200 includes a main body 1210 and a strap 1220. Various parts of the bio-information estimation apparatuses 100 and 500 may be mounted in the main body 1210 and/or may be exposed to the outside thereof.

The main body 1210 may be worn with the strap 1220 around a user's wrist, and the strap 1220 may be formed to be connected at both sides of the main body 1210 to be fastened to each other. The strap 1220 may be made of a flexible material to enable it to bend around a user's wrist so that the main body 1210 may be worn on a user's wrist.

One or more of the main body 1210 and the strap 1220 may include a battery which supplies power to the wearable device 1200.

The wearable device 1200 may further include a spectrometric sensor which is mounted at the main body 1210 to measure a spectrum on a portion of a user's wrist. The spectrometric sensor may include a light source and a detector. The light source of the spectrometric sensor may be provided at the bottom of the main body 1210 to be exposed to the wrist to emit light onto the wrist. Further, the detector may include a photodiode, and may obtain a spectrum by detecting light reflected from the user's skin. The light source or the detector may be an array of one or more light sources or detectors.

Further, the wearable device 1200 may include a temperature sensor mounted in the main body 1210 to measure temperature a portion of a user's wrist. The temperature sensor may measure the temperature while the spectrometric sensor obtains the a spectrum at a portion of a user's wrist.

A processor mounted in the main body 1210 may receive a user command input through a manipulator 1215 or a display 1214, and may perform an operation according to the received command. For example, the processor may be electrically connected with the spectrometric sensor or the temperature sensor; and upon receiving a command from a user to estimate bio-information, the processor may generate a control signal to control the spectrometric sensor or the temperature sensor, and may transmit the generated control signal to the spectrometric sensor or the temperature sensor, as appropriate. The processor may estimate bio-information by receiving the obtained spectrum and temperature information from the spectrometric sensor or the temperature sensor respectively, and by applying a bio-information measuring model.

The processor may calculate a correction factor by inputting the temperature which is measured at the time of measuring the spectrum and is received from the temperature sensor, into a correction factor calculation formula. Further, the processor may correct the spectrum measured by the spectrometric sensor by using the calculated correction factor, and may estimate the bio-information by using the adjusted spectrum. In the case in which a user wears the main body 1210 on the wrist for a long period of time, or in the case in which the light source is driven for a long period of time, emitting light onto a portion of the wrist, the temperature at the wrist may change due to the heat generated by the light source or the user himself. Accordingly, in order to reflect the distortion of the spectrum caused by the temperature change of the object being examined, the measured spectrum may be adjusted to correspond to a spectrum measured at the reference temperature, based on temperature at the time of measuring the spectrum, thereby improving the accuracy of estimation of the bio-information.

In the case in which the bio-information estimation model applied to the wearable device 1200 is an algorithm using the measured spectrum along with the reference spectrum, the processor may correct either one of the reference spectrum and the measured spectrum with reference to a predetermined criterion, and may estimate bio-information based on the adjusted spectrum and the unadjusted spectrum.

The wearable device 1200 may further include a communicator which is mounted at the main body 1210. The communicator may communicate with an external device through wired or wireless communications by the control of the processor, and may receive information such as a reference spectrum and the like, from the external device. Alternatively, the communicator may provide a processing result of the processor to a user by transmitting the processing result to an external device, such as, for example, an external device with better computing performance than that of the processor. The external device may be one of an information processing device, such as a smartphone, a tablet PC, a desktop computer, a laptop computer, and the like, which has a relatively high computing performance.

The wearable device 1200 may further include a display 1214 which is mounted at the top of the main body 1210 and provides a processing result of the processor to a user. For example, the display 1214 may output an estimation result of the bio-information, and in response to a user's request, and/or the display 1214 may output spectrum information, the correction factor, warning information, and the like which are used for the estimation of bio-information. Further, the display 1214 may display an interface to receive various commands from a user or to guide a user, and may transmit information, input through the interface, to the processor. The display 1214 may be formed as a touch screen panel enabling touch input.

The wearable device 1200 may further include a manipulator 1215 which is mounted at the main body 1210. The manipulator 1215 may be exposed to the outside at one side of the main body 1210, may receive a command input from a user, and may transmit the received command to the processor. The manipulator 1215 may have the function of turning the wearable device on/off 1200.

Exemplary embodiments described herein may be realized as a computer-readable code written on a computer-readable recording medium. The computer-readable recording medium may be any type of non-transitory recording device in which data is stored in a computer-readable manner.

Examples of the computer-readable recording medium include a read-only memory (ROM), a random access memory (RAM), a compact disk (CD)-ROM, a magnetic tape, a floppy disc, and an optical data storage. The computer-readable recording medium can be distributed over a plurality of computer systems connected to a network so that a computer-readable code is written thereto and executed therefrom in a decentralized manner. Functional programs, codes, and code segments needed for realizing the exemplary embodiments can be easily deduced by one of ordinary skill in the art.

Exemplary embodiments been described herein. However, it will be obvious to those skilled in the art that various modifications can be made to the exemplary embodiments. Therefore, it is to be understood that that the scope of the above-mentioned exemplary embodiments is not limiting, but is intended to include various modifications and equivalents included within the spirit and scope of the appended claims.

What is claimed is:

1. A bio-information estimation apparatus, comprising:
   a spectrum measurer configured to measure a spectrum of light reflected from a skin of an object;
   a temperature measurer configured to measure a temperature of the object while the spectrum measurer measures the spectrum; and a processor configured to calculate a spectrum correction factor, comprising at least one of a correction factor of a gain, a correction factor of a constant, and a correction factor of a slope, based on the measured temperature of the object, and to adjust the measured spectrum of the skin based on the calculated correction factor, wherein the processor is further configured to:

calculate the correction factor by inputting the measured temperature into a correction factor calculation formula, the correction factor calculation formula representing a correlation between one of a spectrum of light reflected from the skin at a reference temperature and a standard solution at the reference temperature, and a spectrum of light reflected from the skin at a temperature different from the reference temperature; and apply the correction factor to at least one of a gain, a constant, and a slope of the measured spectrum, to obtain the adjusted measured spectrum of the skin.

2. The apparatus of claim 1, wherein the spectrum measurer comprises:

a light source configured to emit light onto the object; and a detector configured to detect light reflected from the object.

3. The apparatus of claim 2, wherein the spectrum measurer measures the spectrum of the skin by using at least one of Infrared spectroscopy and Raman spectroscopy.

4. The apparatus of claim 1, further comprising an output configured to output alarm information in response to at least one of the temperature measurer failing to measure temperature and the measured temperature falling outside a threshold range.

5. The apparatus of claim 1, wherein the processor is further configured to estimate bio-information of the object by applying a bio-information measuring model to the adjusted spectrum.

6. The apparatus of claim 5, wherein the bio-information comprises at least one of blood glucose, cholesterol, triglyceride, protein, and uric acid.

7. The apparatus of claim 5, further comprising an output configured to output at least one of the measured spectrum, the measured temperature, the estimated bio-information, and warning information generated in response to the estimated bio-information.

8. A bio-information estimation method, comprising:

simultaneously measuring a spectrum of light reflected from a skin of an object, and measuring a temperature of the object;

calculating a spectrum correction factor, comprising at least one of a correction factor of a gain, a correction factor of a constant, and a correction factor of a slope, based on the measured temperature of the object; and adjusting the measured spectrum of the skin based on the calculated correction factor, wherein the calculating comprises calculating the correction factor by inputting the measured temperature into a correction factor calculation formula, the correction factor calculation formula representing a correlation between one of a spectrum of light reflected from the skin at a reference temperature and a standard solution at the reference temperature, and a spectrum of light reflected from the skin at a temperature different from the reference temperature, and wherein the adjusting comprises applying the correction factor to at least one of a gain, a constant, and a slope of the measured spectrum, to obtain the adjusted measured spectrum of the skin.

9. The method of claim 8, further comprising outputting alarm information in response to at least one of a failure to measure the temperature and the measured temperature falling outside a threshold range.

10. The method of claim 8, further comprising estimating bio-information of the object by applying a bio-information measuring model to the adjusted spectrum.

11. The method of claim 10, further comprising outputting at least one of the measured spectrum, the measured temperature of the object, the estimated bio-information, and warning information generated in response to the estimated bio-information.

12. A bio-information estimation apparatus, comprising:

a spectrum measurer configured to measure a spectrum of light reflected from a skin of an object;

a temperature measurer configured to measure a temperature of the object while the spectrum measurer measures the spectrum; and a processor configured to calculate a spectrum correction factor, comprising at least one of a correction factor of a gain, a correction factor of a constant, and a correction factor of a slope, based on the measured temperature of the object, to adjust one of the measured spectrum of the skin and a reference spectrum based on the calculated correction factor; and to estimate bio-information of the object based on the adjusted spectrum and an uncorrected one of the measured spectrum and the reference spectrum, wherein the processor is further configured to:

calculate the correction factor by inputting the measured temperature into a correction factor calculation formula, the correction factor calculation formula representing a correlation between one of a spectrum of light reflected from the skin at a reference temperature and a standard solution at the reference temperature, and a spectrum of light reflected from the skin at a temperature different from the reference temperature; and apply the correction factor to at least one of a gain, a constant, and a slope of the one of the measured spectrum of the skin and the reference spectrum.

13. The apparatus of claim 12, further comprising an output configured to output at least one of the measured spectrum, the measured temperature of the object, the estimated bio-information, and warning information generated in response to the estimated bio-information.

14. The apparatus of claim 12, further comprising a storage storing at least one of the measured spectrum, the measured temperature of the object, the estimated bio-information, warning information generated in response to the estimated bio-information, and information about the reference spectrum.

15. The apparatus of claim 12, further comprising a communicator configured to receive the reference spectrum from an external device.

16. The apparatus of claim 12, wherein the reference spectrum is a spectrum measured at the reference temperature from the standard solution including a component related to the bio-information.

* * * * *